(12) United States Patent
Takakura et al.

(10) Patent No.: US 8,691,191 B2
(45) Date of Patent: Apr. 8, 2014

(54) O/W EMULSIFIED COMPOSITION

(75) Inventors: Tomiko Takakura, Yokohama (JP);
Takafumi Kurosawa, Yokohama (JP);
Isao Yajima, Yokohama (JP); Nozomi Fujiyama, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 36 days.

(21) Appl. No.: 13/125,982

(22) PCT Filed: Oct. 27, 2009

(86) PCT No.: PCT/JP2009/068394
§ 371 (c)(1),
(2), (4) Date: Apr. 26, 2011

(87) PCT Pub. No.: WO2010/050464
PCT Pub. Date: May 6, 2010

(65) Prior Publication Data
US 2011/0206628 A1    Aug. 25, 2011

(30) Foreign Application Priority Data

Oct. 31, 2008  (JP) .................. 2008-282274
Oct. 31, 2008  (JP) .................. 2008-282275

(51) Int. Cl.
*A61K 8/06* (2006.01)
*A61K 8/86* (2006.01)
*A61K 8/90* (2006.01)
*A61Q 17/04* (2006.01)

(52) U.S. Cl.
USPC ............................ 424/60; 424/59

(58) Field of Classification Search
None
See application file for complete search history.

(56) References Cited

U.S. PATENT DOCUMENTS

| | | | |
|---|---|---|---|
| 6,416,748 B1 | 7/2002 | Candau et al. | |
| 6,423,302 B1 | 7/2002 | Gers-Barlag et al. | |
| 7,381,403 B2 | 6/2008 | Simonnet | |
| 2003/0180335 A1 | 9/2003 | Ohmori et al. | |
| 2004/0047817 A1 | 3/2004 | Bonda | |
| 2004/0047818 A1 | 3/2004 | Bonda | |
| 2004/0151793 A1* | 8/2004 | Paspaleeva-kuhn et al. | . 424/754 |
| 2004/0166072 A1 | 8/2004 | Bonda | |
| 2009/0028913 A1 | 1/2009 | Takakura | |
| 2009/0280075 A1 | 11/2009 | Flösser-Müller | |
| 2010/0209365 A1 | 8/2010 | Takakura et al. | |
| 2010/0233103 A1 | 9/2010 | Shirao et al. | |

FOREIGN PATENT DOCUMENTS

| | | |
|---|---|---|
| JP | 2001-199857 | 7/2001 |
| JP | 2004-107255 | 4/2004 |
| JP | 2004-352678 | 12/2004 |
| JP | 2007-204459 | 8/2007 |
| JP | 2007-246521 | 9/2007 |
| WO | 2005/082325 | 9/2005 |
| WO | WO 2007013484 A1 * | 2/2007 |
| WO | 2007/122822 A2 | 11/2007 |
| WO | WO 2007122822 A2 * | 11/2007 |
| WO | 2007/147785 A1 | 12/2007 |

OTHER PUBLICATIONS

Watson Loh, Block Copolymer Micelles, Encyclopedia of Surface and Colloid Science, 2002, pp. 802-813.*
Machine translation of WO 2007/013484.*
"Polyoxyethylene Fatty Acid Esters", downloaded on Jun. 5, 2013, from the site: http://www.drugfuture.com/chemdata/polyoxyethylene-fatty-acid-esters.html; 1 page.*
Japanese Patent Abstract for Publication No. 2004-352678 published Dec. 16, 2004, 16 pages.
Japanese Patent Abstract for Publication No. 2004-107255 published Apr. 8, 2004, 19 pages.
International Search Report for corresponding PCT/JP2009/068394 mailed Dec. 22, 2009, two pages.

* cited by examiner

*Primary Examiner* — Brian Gulledge
*Assistant Examiner* — Michael P Cohen
(74) *Attorney, Agent, or Firm* — Rankin, Hill & Clark LLP

(57) ABSTRACT

The present invention provides an O/W emulsified composition which contains an organic UV absorber in an oil state such as octocrylene and a solid organic UV absorber, and is excellent in UV protection ability, formulation stability, and feeling in use. The composition according to the present invention is an O/W emulsified composition, comprising: (a) an organic UV absorber in an oil state at 20° C., comprising (a1) octocrylene; (b) an organic UV absorber in a solid state at 20° C., selected from (b1) bis-ethylhexyloxyphenol methoxyphenyl triazine and (b2) methylene bis-benzotriazolyl tetramethylbutylphenol; and (c) a polyoxyethylene/polyoxyalkylene alkyl ether block polymer represented by formula (1) or (2):

$$R_1O-(PO)m\text{-}(EO)n\text{-}H \quad (1)$$

wherein $R_1$ is a hydrocarbon group having 16 to 18 carbon atoms; PO is an oxypropylene group, EU is an oxyethylene group, and PO and EO are added to each other in block form; and m and n respectively represent average addition mole number of PO and EO, 70>m>4, 70>n>10, and n>m;

$$R_2O\text{-}(AO)p\text{-}(EO)q\text{-}R_3 \quad (2)$$

wherein $R_2$ and $R_3$ are either identical to or different from each other, and each of them is a hydrocarbon group having 1 to 4 carbon atoms; AO is an oxyalkylene group having 3 to 4 carbon atoms, EO is an oxyethylene group, and AO and EO are added to each other in block form; and p and q respectively represent average addition mole number of AO and EO, 1≤p≤70, 1≤q≤70, and 0.2<(q/(p+q))<0.8, and wherein average particle size of the oil phase comprising the component (a) is 700 nm or less.

14 Claims, No Drawings

O/W EMULSIFIED COMPOSITION

RELATED APPLICATIONS

This application claims the priority of Japanese Patent Application Nos. 2008-282274 and 2008-282275 filed on Oct. 31, 2008, which are incorporated herein by reference.

FIELD OF THE INVENTION

The present invention relates to an oil-in-water (O/W) emulsified composition and, in particular, to an O/W emulsified composition which contains an oil-soluble organic UV absorber in an oil state at ordinary temperature together with an organic UV absorber in a solid state at ordinary temperature, and is excellent in formulation stability and feeling in use and suitable as a sunscreen cosmetic.

BACKGROUND OF THE INVENTION

Recently, the effect of ultraviolet on the skin has become widely known recently, and users have become increasingly conscious of skin whitening. Thus, there is demand for a cosmetic which provides a higher UV protection ability and even a good feeling in use.

Due to the fact that an O/W emulsified composition can provide refreshing and light fresh feeling in use while it contains oils, such emulsified composition is widely used not only in cosmetics for basic skin care such as milky lotions and creams, but also in products such as foundations and sunscreen cosmetics.

In cosmetics, UV protection ability has been often provided by incorporating organic UV absorbers or inorganic UV scatterers such as fine particle titanium oxide and fine particle zinc oxide. However, when a high UV protection ability is tried to be provided over a wide range of UV-B to UV-A by incorporating a large amount of inorganic UV shielding powder such as fine particle titanium oxide and fine particle zinc oxide, the finish may become whitish, or frictional or powdery feeling may be caused.

In contrast, many organic UV absorbers are generally highly polar oils and do not cause the problems such as the whitish finish and frictional or powdery feeling mentioned above. However, they provide stickiness so much to deteriorate the refreshing feeling of O/W emulsified composition when the emulsified composition is applied to skin. In addition, the emulsion stability tends to decrease. In particular, when octocrylene and ethylhexyl methoxycinnamate are used in combination as organic UV absorbers, an excellent UV protection ability can be achieved, but it has been difficult to obtain an O/W emulsified composition with a high emulsion stability and a good feeling in use.

Bis-ethylhexyloxyphenol methoxyphenyl triazine is a highly excellent organic UV absorber because of its UV absorbing ability in a wide range of UV-A to UV-B. However, it is essentially a crystalline solid at ordinary temperature, and there has been a problem that it precipitated over time when it was dissolved in the oil phase to prepare an O/W emulsified composition.

Methylene bis-benzotriazolyl tetramethylbutylphenol is a solid organic UV absorber which is essentially insoluble in water and oils, and it generally shows its UV protection ability by being dispersed, in the from of fine particle powder, in products such as cosmetics. Though methylene bis-benzotriazolyl tetramethylbutylphenol is a highly excellent organic UV absorber because of its UV absorbing ability in a wide range from UV-A to UV-B, it is desired to be used in combination with other UV absorbers so as to achieve higher UV protection ability.

However, when methylene bis-benzotriazolyl tetramethylbutylphenol is dispersed in the aqueous phase of an O/W emulsified composition containing, in the oil phase, octocrylene which is an organic UV absorber in an oil state at ordinary temperature, the fine particle powder of methylene bis-benzotriazolyl tetramethylbutylphenol coarsens (agglutinates) over time in water to cause a decreased UV protection ability or a rough feeling in use problematically. Also, as octocrylene is highly polar, there has been a problem that octocrylene was difficult to be emulsified stably in water, and furthermore provided significant stickiness.

Patent Literature 1 suggests that fine particles of an insoluble UV absorber, such as methylene bis-benzotriazolyl tetramethylbutylphenol is incorporated in an emulsion with use of a crosspolymer of ethylenically unsaturated monomers, without using an emulsifier to stability over time and water.

However, even such a method could not achieve sufficient feeling in use or formulation stability.

Patent Literature 2 describes an O/W emulsified composition in which fine particles of methylene bis-benzotriazolyl tetramethylbutylphenol is dispersed in the aqueous phase with, as an emulsifier, a copolymer of polyacrylic acid and alkyl acrylate, or a nonionic surfactant with HLB of 8 or more and/or a fatty acid soap.

However, it does not investigate the inhibition of coarsening or precipitation of fine particles of methylene bis-benzotriazolyl tetramethylbutylphenol in case where octocrylene is incorporated.

PRIOR ART

Patent Literature

Patent Literature 1: Japanese Unexamined Patent Publication No. 2001-199857
Patent Literature 2: Japanese Unexamined Patent Publication No. 2004-107255

DISCLOSURE OF THE INVENTION

Problem to be Solved by the Invention

The present invention has been made in view of the background, and an object of the invention is to provide an O/W emulsified composition which contains an organic UV absorber in an oil state such as octocrylene together with a solid organic UV absorber, and is excellent in UV protection ability, formulation stability, and non-sticky and refreshing feeling in use.

Means to Solve the Problem

To solve the aforementioned problems, the present inventors have diligently studied and found that the problems can be solved by allowing the average particle size of the oil phase containing an organic UV absorber in an oil state to have a certain emulsion particle size or less with use of a specific ingredient as an emulsifier.

For example, the present inventors have found that an O/W emulsified composition which is excellent in UV protection ability and formulation stability over time and has non-sticky and refreshing feeling in use can be obtained by dissolving bis-ethylhexyloxyphenol methoxyphenyl triazine in the oil phase containing octocrylene and ethylhexyl methoxycinnamate, and allowing the oil phase to have a certain emulsion particle size or less with use of a specific ingredient as an emulsifier.

The present inventors also have found that, in case of allowing the oil phase containing octocrylene to have a certain emulsion particle size or less with use of a specific ingredient as an emulsifier, even when fine particles of methylene bis-benzotriazolyl tetramethylbutylphenol are dispersed in the aqueous phase, the coarsening, aggregation or precipitation of the fine particles over time as well as the separation of oil phase do not occur; hence, the obtained O/W emulsified composition has significantly high formulation stability and provides non-sticky and refreshing feeling in use, as well as its UV protection ability or feeling in use is not deteriorated over time, thus leading to completion of the present invention.

The present invention provides an O/W emulsified composition, comprising:
(a) an organic UV absorber in an oil state at 20° C., comprising (a1) octocrylene;
(b) an organic UV absorber in a solid state at 20° C., selected from
(b1) bis-ethylhexyloxyphenol methoxyphenyl triazine and
(b2) methylene bis-benzotriazolyl tetramethylbutylphenol; and
(c) a polyoxyethylene/polyoxyalkylene alkyl ether block polymer represented by formula (1) or (2):

$$R_1O\text{—}(PO)m\text{-}(EO)n\text{—}H \quad (1)$$

wherein $R_1$ is a hydrocarbon group having 16 to 18 carbon atoms; PO is an oxypropylene group, EU is an oxyethylene group, and PO and EO are added to each other in block form; and m and n respectively represent average addition mole number of PO and EU, 70>m>4, 70>n>10, and n>m;

$$R_2O\text{-}(AO)p\text{-}(EO)q\text{—}R_3 \quad (2)$$

wherein $R_2$ and $R_3$ are either identical to or different from each other, and each of them is a hydrocarbon group having 1 to 4 carbon atoms; AO is an oxyalkylene group having 3 to 4 carbon atoms, EO is an oxyethylene group, and AO and EO are added to each other in block form; and p and q respectively represent average addition mole number of AO and EO, 1≤p≤70, 1≤q≤70, and 0.2<(q/(p+q))<0.8, and
wherein average particle size of the oil phase comprising the component (a) is 700 nm or less.

Also, the present invention provides the O/W emulsified composition, wherein:
the component (a) further comprises (a2) ethylhexyl methoxycinnamate;
the component (b) comprises the component (b1) bis-ethylhexyloxyphenol methoxyphenyl triazine; and
the components (a) and (b1) are dissolved in the oil phase.

Also, the present invention provides the O/W emulsified composition, wherein:
the component (b) comprises the component (b2) methylene bis-benzotriazolyl tetramethylbutylphenol; and
the component (b2) is dispersed in the aqueous phase.

Also, the present invention provides the O/W emulsified composition, wherein, as the component (b2), an aqueous dispersion wherein methylene bis-benzotriazolyl tetramethylbutylphenol is finely dispersed with alkylpolyglucoside is used.

Also, the present invention provides the O/W emulsified composition, wherein the component (b2) is 0.5 to 10% by mass in the composition.

Also, the present invention provides the O/W emulsified composition, wherein the component (a) further comprises the component (a2) ethylhexyl methoxycinnamate.

Also, the present invention provides the O/W emulsified composition, wherein:
the component (b) comprises the component (b1) bis-ethylhexyloxyphenol methoxyphenyl triazine in addition to the component (b2) methylene bis-benzotriazolyl tetramethylbutylphenol; and
the component (b1) is dissolved in the oil phase.

Also, the present invention provides the O/W emulsified composition, wherein the organic UV absorbers is 8% by mass or more in total in the composition.

Also, the present invention provides the O/W emulsified composition, wherein the component (c) is 0.3 to 3% by mass in the composition.

Also, the present invention provides a sunscreen cosmetic, consisting of any of the above-mentioned O/W emulsified compositions.

Effect of the Invention

According to the present invention, the O/W emulsified composition which contains an organic UV absorber that is essentially in an oil state at ordinary temperature and an organic UV absorber that is essentially solid at ordinary temperature, and is excellent in UV protection ability, formulation stability, and feeling in use and suitable for a sunscreen cosmetic can be obtained.

For example, bis-ethylhexyloxyphenol methoxyphenyl triazine is dissolved in an oil phase containing octocrylene and ethylhexyl methoxycinnamate, and then the oil phase is emulsified finely with use of a specific emulsifier to be a certain emulsion particle size or less, whereby an O/W emulsified composition which shows high UV protection ability in a wide UV range and is also excellent in formulation stability and feeling in use can be obtained. The emulsified composition can contain a large amount of organic UV absorbers and is very useful for a sunscreen cosmetic and so on.

Also, an oil phase containing octocrylene is emulsified finely with use of a specific emulsifier to be a certain emulsion particle size or less fine particles of methylene bis-benzotriazolyl tetramethylbutylphenol is dissolved in the aqueous phase of an O/W emulsified composition which is obtained by, whereby an O/W emulsified composition excellent in formulation stability as well as feeling in use can be obtained.

The emulsified composition of the present invention can contain a large amount of organic UV absorbers and is very useful as a sunscreen cosmetic.

BEST MODE FOR CARRYING OUT THE INVENTION (a) Organic UV Absorber in Oil State

Among the organic UV absorbers in an oil state at ordinary temperature (about 20° C.) used in the present invention, as (a1) octocrylene (chemical name: 2-ethylhexyl 2-cyano-3,3-diphenylacrylate), commercially available products such as "Uvinul N539" (manufactured by BASF) or "Parsol 340" (manufactured by DSM Nutrition Japan K.K.) can be easily used.

The amount of octocrylene can be suitably set depending on purposes. From a viewpoint of UV protection ability or solubility of solid components, the amount of octocrylene is preferably 1% by mass or more, more preferably 2% by mass or more, and particularly preferably 3% by mass or more, in the O/W emulsified composition of the present invention. On the other hand, when octocrylene is contained excessively, the feeling in use is deteriorated with stickiness and an oily feeling. Thus, the amount is preferably 10% by mass or less, more preferably 8% by mass or less, and particularly preferably 6% by mass or less, in the O/W emulsified composition of the present invention.

(a2) Ethylhexyl methoxycinnamate (octyl methoxycinnamate) is an UV absorber which is in an oil state at ordinary temperature, and commercially available products such as "Parsol MCX" (manufactured by DSM Nutrition Japan K.K.) can be easily used.

The amount of ethylhexyl methoxycinnamate can be suitably set depending on purposes. From a viewpoint of UV protection ability or solubility of solid components, the amount of ethylhexyl methoxycinnamate is preferably 1% by mass or more, more preferably 2% by mass or more, and particularly preferably 4% by mass or more, in the O/W emulsified composition of the present invention. On the other hand, when ethylhexyl methoxycinnamate is contained excessively, the feeling in use is deteriorated with stickiness and an oily feeling. Thus, the amount is preferably 7.5% by mass or less, more preferably 7% by mass or less, and particularly preferably 6% by mass or less, in the O/W emulsified composition of the present invention.

In this context, like octocrylene, ethylhexyl methoxycinnamate also tends to cause the aggregation of the poorly soluble solid organic UV absorber, that is (b2) methylene bis-benzotriazolyl tetramethylbutylphenol described below. However, in the present invention, even when ethylhexyl methoxycinnamate is incorporated in the oil phase in addition to octocrylene, the O/W emulsified composition excellent in formulation stability and feeling in use can be obtained.

(b) Solid Organic UV Absorber

Among the organic UV absorbers in a solid state at ordinary temperature (about 20° C.) used in the present invention, as (b1) bis-ethylhexyloxyphenol methoxyphenyl triazine (chemical name: 2,4-bis-{[4-(2-ethylhexyloxy)-2-hydroxy]-phenyl}-6-(4-methoxyphenyl)-(1,3,5)-triazine)), commercially available products such as "Tinosorb S" (manufactured by Ciba Specialty Chemicals Inc.) can be easily used.

The amount of bis-ethylhexyloxyphenol methoxyphenyl triazine can be suitably set depending on purposes. From a viewpoint of UV protection ability and so on, the amount of bis-ethylhexyloxyphenol methoxyphenyl triazine is preferably 0.5% by mass or more, more preferably 1% by mass or more, and particularly preferably 1.5% by mass or more, in the O/W emulsified composition of the present invention. On the other hand, when bis-ethylhexyloxyphenol methoxyphenyl triazine is contained excessively, it makes easier to cause precipitation of crystals over time. Thus, the amount is preferably 5% by mass or less, more preferably 4% by mass or less, and particularly preferably 3% by mass or less, in the O/W emulsified composition of the present invention.

In the O/W emulsified composition of the present invention, bis-ethylhexyloxyphenol methoxyphenyl triazine is dissolved in the oil phase containing the component (a).

Though bis-ethylhexyloxyphenol methoxyphenyl triazine is usually used by being dissolved in a highly polar oil, it can be is dissolve also in octocrylene or ethylhexyl methoxycinnamate. When bis-ethylhexyloxyphenol methoxyphenyl triazine is used by being dissolved in the oil phase of the O/W emulsified composition of the present invention, it can keep dissolving therein stably.

As (b2) methylene bis-benzotriazolyl tetramethylbutylphenol (chemical name: 2,2'-methylene bis(6-(2H-benzotriazole-2-yl)-4-(1,1,3,3-tetramethylbutyl)phenol)), a fine dispersion thereof in the aqueous phase can be used. As a surfactant preferable for dispersing it, an alkylpolyglucoside represented by $C_nH_{2n+1}O(C_6H_{10}O_5)_xH$, wherein n is any integer of 8 to 16, and x represents the average polymerization degree of glucoside units and is in the range of 1.4 to 1.6, has been known (see Patent Literature 1, Japanese Unexamined Patent Publication No. 2000-501064, etc.). For example, 50% dispersion of the fine particles of 300 nm or less in the aqueous phase is commercially available as "Tinosorb M" or "Tinosorb M1" (manufactured by Ciba Specialty Chemicals Inc.), which can be easily used.

The amount of methylene bis-benzotriazolyl tetramethylbutylphenol can be suitably set depending on purposes. From a viewpoint of UV protection ability and so on, the amount of methylene bis-benzotriazolyl tetramethylbutylphenol is preferably 0.5% by mass or more, and more preferably 1% by mass or more, in dry mass in the O/W emulsified composition of the present invention. On the other hand, when methylene bis-benzotriazolyl tetramethylbutylphenol is contained excessively, the precipitation over time tends to be concerned. Thus, the amount is preferably 10% by mass or less, more preferably 6% by mass or less, and particularly preferably 4% by mass or less, in the O/W emulsified composition of the present invention.

In the O/W emulsified composition of the present invention, methylene bis-benzotriazolyl tetramethylbutylphenol is localized in the aqueous phase as fine particle powder. For example, 80% by mass or more, or even 90% by mass or more is present in the aqueous phase, and it is scarcely present in the oil phase. The dispersed particle size is usually 1 μm or less, and preferably 500 nm or less. When the dispersed particle size is larger, the UV protection ability decreases, and even the aggregation is caused.

The total amount of the organic UV absorbers can be set depending on a desired UV protection ability, and it is preferably 8% by mass or more, more preferably 9% by mass or more, and particularly preferably 10% by mass or more, in the O/W emulsified composition. In the present invention, even when such a large amount of oil-soluble organic UV absorber is incorporated, the O/W emulsified composition excellent in formulation stability and feeling in use can be obtained. Though the upper limit is not restricted in particular, it is usually 30% by mass or less, and preferably 25% by mass or less.

(c) Polyoxyethylene/Polyoxyalkylene Alkyl Ether Block Polymer

In the present invention, as an emulsifier for the oil phase containing the component (a), one or more polyoxyethylene/polyoxyalkylene alkyl ether block polymers represented by the following formula (1) or (2) are preferably used. With the use of the emulsifier, the O/W emulsified composition in which the oil phase containing the component (a) is finely and stably emulsified can be easily produced. In the oil phase to be emulsified with the emulsifier, an oil-soluble organic UV absorber such as the component (b1) and other oils may be contained.

$$R_1O-(PO)m\text{-}(EO)n-H \qquad (1)$$

In the formula (1), $R_1$ is a hydrocarbon group having 16 to 18 carbon atoms, and it is preferably a saturated or unsaturated aliphatic hydrocarbon group. The examples include palmityl, stearyl, isostearyl, oleyl, and linolyl groups.

PO is an oxypropylene group, and EO is an oxyethylene group.

In the formula (1), PO and EO must bond to each other in block form. When they bond to each other in random form, the formulation stability cannot be sufficiently achieved. The addition order of propylene oxide and ethylene oxide is not particularly specified. The block includes not only two-stepwise block, but also three- or more-stepwise block.

m and n respectively represent the average addition mole number of PO and EO, 70>m>4, 70>n>10, and n>m.

The molecular weight of the block polymer in the formula (1) is preferably 800 or more, and more preferably 1500 or more. When the molecular weight is less than 800, the effect is low. Though the upper limit of the molecular weight cannot be specified particularly, stickiness tends to be caused as the molecular weight becomes larger.

Examples of the block polymer represented by the formula (1) include Nikkol PBC44 (manufactured by Nikko Chemicals Co., Ltd.)

$$R_2O\text{-}(AO)p\text{-}(EO)q\text{-}R_3 \quad (2)$$

In the formula (2), $R_2$ and $R_3$ are either identical to or different from each other, and each of them is a hydrocarbon group having 1 to 4 carbon atoms and preferably a saturated aliphatic hydrocarbon group. The examples include methyl, ethyl, propyl, isopropyl, butyl, isobutyl, sec-butyl, and tert-butyl groups, and more preferably methyl and ethyl groups.

AO is an oxyalkylene group having 3 to 4 carbon atoms, and the examples include oxypropyl and oxybutyl groups. EO is an oxyethylene group.

In the formula (2), AO and EO bond to each other in block form. When they bond to each other in random form, the formulation stability cannot be sufficiently achieved. The addition order of ethylene oxide and alkylene oxide is not particularly specified. The block includes not only two-stepwise block, but also three- or more-stepwise block.

p and q respectively represent the average addition mole number of AO and EO, $1 \leq p \leq 70$, $1 \leq q \leq 70$, and $0.2 < (q/(p+q)) < 0.8$.

The molecular weight of the block polymer in the formula (2) is preferably 1000 or more, and more preferably 3000 or more. When the molecular weight is less than 1000, the effect is low. Though the upper limit of the molecular weight cannot be specified particularly, stickiness tends to be caused as the molecular weight becomes larger.

The block polymer of the formula (2) can be produced in a known method. For example, after addition polymerization of an ethylene oxide and an alkylene oxide having 3 to 4 carbon atoms with a compound having a hydroxyl group, etherification with an alkyl halide is carried out in the presence of an alkaline catalyst, to obtain the product (see Japanese Unexamined Patent Publication No. 2004-83541, etc.).

Specific examples of the block polymer of the formula (2) include POE (14) POP (7) dimethyl ether, POE (10) POP (10) dimethyl ether, POE (7) POP (12) dimethyl ether, POE (15) POP (5) dimethyl ether, POE (25) POP (25) dimethyl ether, POE (27) POP (14) dimethyl ether, POE (55) POP (28) dimethyl ether, POE (22) POP (40) dimethyl ether, POE (35) POP (40) dimethyl ether, POE (50) POP (40) dimethyl ether, POE (36) POP (41) dimethyl ether, POE (55) POP (30) dimethyl ether, POE (30) POP (34) dimethyl ether, POE (25) POP (30) dimethyl ether, POE (14) POB (7) dimethyl ether, POE (10) POP (10) diethyl ether, POE (10) POP (10) dipropyl ether, and POE (10) POP (10) dibutyl ether.

POE, POP, and POB respectively stand for polyoxyethylene, polyoxypropylene, or polyoxybutylene. Hereinafter they may be referred to with these abbreviations.

As even a small amount of these block polymers can emulsify finely and stably the oil phase containing the component (a), the stable O/W emulsified composition without stickiness owing to surfactants can be obtained. However, when the amount of block polymer is too small, the stable O/W emulsified composition cannot be obtained. Thus, the amount is preferably 0.3 to 3% by mass, more preferably 0.3 to 2% by mass, and particularly preferably 0.3 to 1% by mass, in the composition.

O/W Emulsified Composition

In the O/W emulsified composition of the present invention, the average emulsion particle size of the oil phase is to be 700 nm or less. When the particle size exceeds 700 nm, the formulation stability or the feeling in use is deteriorated.

Any emulsification method can be used for the first oil phase so far as the oil phase can be emulsified so finely as to be 700 nm or less. The examples include a high-pressure emulsification method and a microemulsification method using a hydrophilic solvent such as a polyhydric alcohol in the presence of a small amount of water (or in the absence of water) (see Japanese Examined Patent Publication No. S57-29213, Japanese Unexamined Patent Publication No. 2006-182724, etc.); however, they are not limited thereto.

When (b1) bis-ethylhexyloxyphenol methoxyphenyl triazine is used as the component (b), the O/W emulsified composition of the present invention is preferably a composition that the oil phase particles having the average particle size of 700 nm or less and containing octocrylene, ethylhexyl methoxycinnamate, and bis-ethylhexyloxyphenol methoxyphenyl triazine are dispersed in the aqueous phase which is a continuous phase, and that the oil phase is a homogenous phase in which bis-ethylhexyloxyphenol methoxyphenyl triazine is dissolved.

The production method is not limited in particular, and the O/W emulsified composition can be typically produced by emulsifying, with use of (c) polyoxyethylene/polyoxyalkylene alkyl ether block polymer, the aqueous phase and the oil phase in which (a1) octocrylene, (a2) ethylhexyl methoxycinnamate, and (b1) bis-ethylhexyloxyphenol methoxyphenyl triazine are mixed and dissolved. As far as any problem is not caused in particular, other ingredients may be incorporated in the oil or aqueous phase depending on their compatibility or affinity.

When (b2) methylene bis-benzotriazolyl tetramethylbutylphenol is used as the component (b), the O/W emulsified composition of the present invention is a composition that
(i) oil phase particles having the average particle size of 700 nm or less and containing octocrylene, and
(ii) fine particles of methylene bis-benzotriazolyl tetramethylbutylphenol are dispersed in a substantially separate state in the aqueous phase which is a continuous phase.

The production method is not limited in particular, and the O/W emulsified composition can be typically produced by emulsifying, with use of (c) polyoxyethylene/polyoxyalkylene alkyl ether block polymer, the oil phase containing (a1) octocrylene and the aqueous phase in which fine particles of (b2) methylene bis-benzotriazolyl tetramethylbutylphenol are dispersed. Alternatively, it also can be produced by emulsifying the oil phase containing (a1) octocrylene with use of (c) polyoxyethylene/polyoxyalkylene alkyl ether block polymer to prepare an O/W emulsified composition, and then adding an aqueous dispersion solution of (b2) methylene bis-benzotriazolyl tetramethylbutylphenol thereto. As far as any problem is not caused in particular, other ingredients may be incorporated in the oil or aqueous phase depending on their compatibility or affinity.

In the O/W emulsified composition of the present invention, the average emulsion particle size of the oil phase containing the component (a) is to be 700 nm or less. When the particle size exceeds 700 nm, the feeling in use becomes poor, and the formulation stability decreases (e.g., coarsening, aggregation, and precipitation of dispersed fine particles of methylene bis-benzotriazolyl tetramethylbutylphenol, in addition to oil separation or creaming over time).

In the O/W emulsified composition of the present invention, other ingredients which can be incorporated in cosmetics can be further contained in addition to the essential components mentioned above so far as the effect of the present invention is not affected. For examples, powders, liquid oils, solid oils, waxes, hydrocarbons, higher fatty acids, higher alcohols, esters, silicones, anionic surfactants, cationic surfactants, amphoteric surfactants, nonionic surfactants, moisturizers, water-soluble polymers, thickeners, film-forming agents, UV absorbers, UV scatterers, metal ion sequestering agents, lower alcohols, polyhydric alcohols, saccharides, amino acids, organic amines, polymer emulsions, pH adjusters, skin nutrients, vitamins, antioxidants, antioxidant aids, perfumes, and water can be suitably incorporated as necessary.

In the O/W emulsified composition of the present invention, organic UV absorbers other than the above-mentioned also can be contained. Examples thereof include UV absorbers generally used in cosmetics: for example, triazine UV absorbers such as bis(resorcinyl)triazine; octyl triazone (2,4, 6-tris-[4-(2- ethylhexyloxycarbonyl)anilino]- 1,3,5-triazine); benzoic acid UV absorbers such as p-aminobenzoic acid (hereinafter abbreviated as "PABA"), PABA monoglycerin ester, N, N-dipropoxy PABA ethyl ester, N, N-diethoxy PABA ethyl ester, N, N-dimethyl PABA butyl ester, and N, N-dimethyl PABA ethyl ester; anthranilic acid UV absorbers such as homomenthyl-N-acetyl anthranilate; salicylic acid UV absorbers such as amyl salicylate, menthyl salicylate, homomenthyl salicylate, octyl salicylate, phenyl salicylate, benzyl salicylate, and p-isopropanol phenyl salicylate; cinnamic acid UV absorbers such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl p-methoxycinnamate (2-ethylhexyl p- methoxycinnamate), 2-ethoxyethyl-p-methoxycinnamate, cyclohexyl-p- methoxycinnamate, ethyl-α-cyano-β-phenylcinnamate, 2-ethylhexyl-α-cyano-β-phenylcinnamate, and glyceryl mono-2-ethylhexanoyl-dipara methoxycinnamate; benzophenone UV absorbers such as 2, 4-dihydroxybenzophenone, 2,2'-dihydroxy-4- methoxybenzophenone, 2,2'-dihydroxy-4, 4'-dimethoxybenzophenone, 2,2',4,4'- tetrahydroxybenzophenone, 2-hydroxy-4-methoxybenzophenone, 2-hydroxy-4-methoxy- 4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy- 4-n-octoxybenzophenone, and 4-hydroxy-3-carboxybenzophenone; 3-(4'- methylbenzylidene)-d, l-camphor; 3-benzylidene-d, l-camphor; 2-phenyl-5-methyl benzoxazole; 2, 2'-hydroxy-5-methylphenyl benzotriazole; 2-(2'-hydroxy-5'-t-octylphenyl) benzotriazole; 2-(2'-hydroxy-5'-methylphenyl)benzotriazole; dibenzaladine; dianisoylmethane; 4-methoxy-4'-t-butyldibenzoylmethane; 5-(3,3-dimethyl-2- norbornylidene)-3-pentane-2-one, and 4,4-diarylbutadiene.

The O/W emulsified composition of the preset invention is applicable in various cosmetics in which sunscreen function is desired. For example, it is applicable in makeup cosmetics such as foundations and lipsticks, as well as milky lotions, creams, and pre-makeup.

EXAMPLES

Hereinafter, the present invention will be further explained with reference to specific examples. However, the present invention is not limited by these examples. The amount is expressed in mass % unless otherwise specified. The evaluation methods used in the present invention are as follows.

(Average Emulsion Particle Size)

The particle size distribution of the O/W emulsified composition just after preparation was measured with Zetasizer Nano ZS (manufactured by Sysmex Corporation).

(Feeling in Use)

In 20 female panelists, each test sample just after preparation was applied to the face by hand and evaluated according to the following criteria with the questionnaire for stickiness during application.

O: 16 or more of panelists answered that there was no stickiness.

Δ: 6 or more to 15 or less of panelists answered that there was no stickiness.

X: 5 or less of panelists answered that there was no stickiness.

(Emulsion Stability)

The appearance of each test sample which had been preserved at 50° C. for one month was observed by the naked eye and evaluated according to the following criteria.

O: There is no oil floatation or creaming.

Δ: There are slight oil floatation and creaming.

X: There are oil floatation and creaming.

(Solubility Stability)

The precipitate in each test sample which had been preserved at 0° C. for one month was observed by the naked eye and evaluated according to the following criteria.

O: Crystals or insoluble matter did not precipitate.

Δ: Crystals and insoluble matter precipitated slightly.

X: Crystals and insoluble matter precipitated.

(Dispersion Stability of Fine Particles)

The precipitate of each test sample which had been preserved at 50° C. for one month was observed by the naked eye and evaluated according to the following criteria.

O: Crystals or insoluble matter did not precipitate.

Δ: Crystals and insoluble matter precipitated slightly.

X: Crystals and insoluble matter precipitated.

(UV Protection Ability)

The UV protection ability of each test sample just after preparation was measured with in vitro SPECTRO PHOTOMETER U-4100 (manufactured by Hitachi, Ltd.) and evaluated according to the following criteria.

O: The absorbance at 310 nm was higher than that of a reference sample showing in vivo measurement value of SPF 16.

X: The absorbance at 310 nm was lower than that of a reference sample showing in vivo measurement value of SPF 16.

Example 1

Particle Size of Oil Phase

O/W compositions containing the (b1) were prepared with the compositions in Table 1 according to the following production method.

TABLE 1

| No. | Components | Test Ex. 1-1 | Test Ex. 1-a |
|-----|------------|--------------|--------------|
| 1 | Water | Balance | Balance |
| 2 | Ethanol | 6 | 6 |
| 3 | Octocrylene | 5 | 5 |
| 4 | Ethylhexyl methoxycinnamate | 5 | 5 |
| 5 | Bis-ethylhexyloxyphenol methoxyphenyl triazine | 2 | 2 |
| 6 | Dipropylene glycol | 3 | 3 |
| 7 | Glycerin | 1 | 1 |

TABLE 1-continued

| | | Production method 1-1 or 1-1' | Production method 1-2 |
|---|---|---|---|
| 8 | POE(20)POP(8)cetyl ether | 0.4 | 0.4 |
| 9 | Isostearic acid | 0.2 | 0.2 |
| 10 | Carbomer K | 0.13 | 0.13 |
| 11 | (Acrylic acid/(C10-30)alkyl acrylate) copolymer * | 0.07 | 0.07 |
| 12 | Trisodium edetate | 0.02 | 0.02 |
| 13 | BHT | 0.004 | 0.004 |
| 14 | Phenoxyethanol | 0.3 | 0.3 |
| 15 | Methyl paraben | 0.15 | 0.15 |

| Production method | Production method 1-1 or 1-1' | Production method 1-2 |
|---|---|---|
| Average emulsion particle size | 614 nm | 2500 nm |
| Feeling in use (stickiness during application) | ○ | Δ |
| Emulsion stability (50° C. × 1M) | ○ | x |
| Solubility stability (0° C. × 1M) | ○ | ○ |

* PEMULEN TR-2: BF Goodrich (Production Method)
Production Method 1-1:
To a part of Component (1), Components (3) to (5) and Component (8) are added with heat, and the mixture is emulsified with a high-pressure emulsification device (manufactured by APV). The other components are added to and mixed with the emulsion to obtain the aimed O/W emulsified composition.
Production Method 1-1':
Components (6), (7), (8), and a part of Component (1) are mixed, and a dissolved mixture of Components (3) to (5) is added thereto. The obtained mixture is emulsified with a homomixer. The other components are added to and mixed with the emulsion to obtain the aimed O/W emulsified composition.
Production Method 1-2:
A dissolved mixture of Components (3) to (5) and (8) is added to a solution in which Component (11) is dissolved in Component (1), and the mixture is emulsified with a homomixer. The other components are added to and mixed with the emulsion to obtain the aimed O/W emulsified composition.

As shown in Table 1, even with the same composition, when the emulsion particle size exceeds 700 nm such as Test Example 1-a, stickiness is felt during application on the skin, and the emulsion stability is not sufficient.

Example 2

Amount of Surfactant

O/W emulsified compositions were prepared in the same method with Test Example 1-1, except for changing the amounts of block polymer POE(20)POP(80)cetyl ether as an emulsifier.

TABLE 2

| Components | Test Ex. 1-1 | Test Ex. 2-a | Test Ex. 2-b |
|---|---|---|---|
| POE(20)POP(8)cetyl ether | 0.4 | 0.2 | 3.1 |
| Average emulsion particle size | 614 nm | 670 nm | 560 nm |
| Feeling in use (stickiness during application) | ○ | ○ | x |
| Emulsion stability (50° C. × 1M) | ○ | Δ | ○ |
| Solubility stability (0° C. × 1M) | ○ | ○ | ○ |

As shown in Table 2, the emulsion stability tends to decrease when the amount of block polymer is too small. When the block polymer is contained excessively, sticky feeling is caused during application.

From these results, the amount of block polymer is preferably 0.3 to 3% by mass, more preferably 0.3 to 2% by mass, and particularly preferably 0.3 to 1% by mass, in the O/W emulsified composition of the present invention.

According to the present invention, as shown in Table 2, it is possible that a large amount of oil-soluble organic UV absorber (e.g., 8% by mass or more) is stably emulsified with use of an extremely small amount of emulsifier (e.g., 1% by mass or less) to provide an O/W emulsified composition excellent in UV protection ability, formulation stability, and feeling in use.

Example 3

Kind of Surfactant

O/W emulsified compositions were prepared in the same method with Test example 1-1, except for changing the kinds of block polymer POE(20)POP(80)cetyl ether as an emulsifier.

TABLE 3

| Components | Test Ex. 1-1 | Test Ex. 3-1 | Test Ex. 3-2 | Test Ex. 3-a | Test Ex. 3-b | Test Ex. 3-c |
|---|---|---|---|---|---|---|
| POE(20)POP(8)cetyl ether [HLB = 12.5] | 0.4 | — | — | — | — | — |
| POE(50)POP(40)dimethyl ether [HLB = 17] | — | 0.4 | — | — | — | — |
| POE(35)POP(40)dimethyl ether [HLB = 12] | — | — | 0.4 | — | — | — |
| POE(30)behenyl ether [HLB = 18] | — | — | — | 0.4 | — | — |
| POE(60)glyceryl isostearate [HLB = 18.3] | — | — | — | — | 0.4 | — |
| POE(60)hydrogenated castor oil [HLB = 14.6] | — | — | — | — | — | 0.4 |
| POE(100)hydrogenated castor oil [HLB = 16.5] | — | — | — | — | — | — |
| POE(30)phytosterol [HLB = 18] | — | — | — | — | — | — |
| POE(30)cholestanol [HLB = 17] | — | — | — | — | — | — |
| POE(20)sorbitan monostearate [HLB = 14.9] | — | — | — | — | — | — |
| POE(20)sorbitan monolaurate [HLB = 16.9] | — | — | — | — | — | — |
| Average emulsion particle size | 614 nm | 604 nm | 690 nm | 1000 nm | 1500 nm | 2000 nm |
| Feeling in use (stickiness during application) | ○ | ○ | ○ | Δ | Δ | Δ |
| Emulsion stability (50° C. × 1M) | ○ | ○ | ○ | Δ | Δ | Δ |
| Solubility stability (0° C. × 1M) | ○ | ○ | ○ | ○ | ○ | ○ |

| Components | Test Ex. 3-d | Test Ex. 3-e | Test Ex. 3-f | Test Ex. 3-g | Test Ex. 3-h |
|---|---|---|---|---|---|
| POE(20)POP(8)cetyl ether [HLB = 12.5] | — | — | — | — | — |
| POE(50)POP(40)dimethyl ether [HLB = 17] | — | — | — | — | — |
| POE(35)POP(40)dimethyl ether [HLB = 12] | — | — | — | — | — |

TABLE 3-continued

| | | | | | |
|---|---|---|---|---|---|
| POE(30)behenyl ether [HLB = 18] | — | — | — | — | — |
| POE(60)glyceryl isostearate [HLB = 18.3] | — | — | — | — | — |
| POE(60)hydrogenated castor oil [HLB = 14.6] | — | — | — | — | — |
| POE(100)hydrogenated castor oil [HLB = 16.5] | 0.4 | — | — | — | — |
| POE(30)phytosterol [HLB = 18] | — | 0.4 | — | — | — |
| POE(30)cholestanol [HLB = 17] | — | — | 0.4 | — | — |
| POE(20)sorbitan monostearate [HLB = 14.9] | — | — | — | 0.4 | — |
| POE(20)sorbitan monolaurate [HLB = 16.9] | — | — | — | — | 0.4 |
| Average emulsion particle size | 1500 nm | 1000 nm | 1100 nm | 3100 nm | 3000 nm |
| Feeling in use (stickiness during application) | Δ | Δ | Δ | x | x |
| Emulsion stability (50° C. × 1M) | Δ | Δ | Δ | x | x |
| Solubility stability (0° C. × 1M) | ○ | ○ | ○ | ○ | ○ |

As shown in Table 3, with the block polymer of the formula (1) or (2), the oil phase containing the component (a) could be easily emulsified to be 700 nm or less, and the O/W emulsified composition excellent in formulation stability and feeling in use could be obtained. However, with the other nonionic surfactants, even when the HLB was in the same range, it was difficult to obtain such an O/W emulsified composition.

Example 4

Amount of Organic UV Absorber

O/W emulsified compositions were prepared in the same method with Test example 1-1, except for changing the amounts of organic UV absorber.

From these results, in the O/W emulsified composition, it is preferred that the amount of octocrylene is 10% by mass or less, the amount of ethylhexyl methoxycinnamate is 7.5% by mass or less, and the amount of bis-ethylhexyloxyphenol methoxyphenyl triazine is 5% by mass or less.

In this context, as shown in Test examples 4-d to 4-f, when the amount of organic UV absorber is too small, the UV protection ability decreases. Thus, the total amount of organic UV absorbers is 8% by mass or more, more preferably 9% by mass or more, and particularly preferably 10% by mass or more.

TABLE 4

| Components | Test Ex. 4-a * | Test Ex. 4-b * | Test Ex. 4-c * | Test Ex. 4-d | Test Ex. 4-e | Test Ex. 4-f |
|---|---|---|---|---|---|---|
| Octocrylene | 11 | 5 | 5 | 0.5 | 4 | 5 |
| Ethylhexyl methoxycinnamate | 5 | 5 | 8 | 5 | 4 | 0.5 |
| Bis-ethylhexyloxyphenol methoxyphenyl triazine | 2 | 6 | 2 | 2 | 0.2 | 2 |
| Average emulsion particle size | 683 nm | 612 nm | 630 nm | 500 nm | 622 nm | 511 nm |
| Feeling in use (stickiness during application) | Δ | Δ | Δ | ○ | ○ | ○ |
| Emulsion stability (50° C. × 1M) | x | x | x | ○ | ○ | ○ |
| Solubility stability (0° C. × 1M) | ○ | x | ○ | x | ○ | x |
| UV protection ability | ○ | ○ | ○ | x | x | x |

* Amount of POE(20)POP(8)cetyl ether is 1% by mass.

As shown in Test examples 4-a to 4-c, when an organic UV absorber is contained excessively, stickiness is caused or the emulsion stability decreases. In addition, when bis-ethylhexyloxyphenol methoxyphenyl triazine is contained excessively, precipitation over time may be caused.

Example 5

Oil Phase Particle Size

O/W emulsified compositions containing the (b2) were prepared with the compositions in Table 5 according to the following production method.

TABLE 5

| No. | Components | Test Ex. 5-1 | Test Ex. 5-2 | Test Ex. 5-a | Test Ex. 5-b |
|---|---|---|---|---|---|
| 1 | Water | Balance | Balance | Balance | Balance |
| 2 | Ethanol | 6 | 6 | 6 | 6 |
| 3 | Octocrylene | 5 | 8 | 5 | 8 |
| 4 | Ethylhexyl methoxycinnamate | 5 | — | 5 | — |
| 5 | Tinosorb M *1 (methylene bis-benzo triazolyl tetramethylbutylphenol) | 8 (4) | 8 (4) | 8 (4) | 8 (4) |
| 6 | Dipropylene glycol | 3 | 3 | 3 | 3 |
| 7 | Glycerin | 1 | 1 | 1 | 1 |
| 8 | POE(20)POP(8)cetyl ether | 0.4 | 0.4 | 0.4 | 0.4 |
| 9 | Isostearic acid | 0.2 | 0.2 | 0.2 | 0.2 |
| 10 | Carbomer K | 0.12 | 0.12 | 0.12 | 0.12 |
| 11 | (Acrylic acid/(C10-30)alkyl acrylate) copolymer *2 | 0.06 | 0.06 | 0.06 | 0.06 |
| 12 | Trisodium edetate | 0.02 | 0.02 | 0.02 | 0.02 |

TABLE 5-continued

| | | | | |
|---|---|---|---|---|
| 13 BHT | 0.004 | 0.004 | 0.004 | 0.004 |
| 14 Phenoxyethanol | 0.3 | 0.3 | 0.3 | 0.3 |
| 15 Methyl paraben | 0.15 | 0.15 | 0.15 | 0.15 |

| Production method | Production method 2-1 or 2-1' | Production method 2-1 or 2-1' | Production method 2-2 | Production method 2-2 |
|---|---|---|---|---|
| Average emulsion particle size | 614 nm | 580 nm | 1000 nm | 1000 nm |
| Feeling in use (stickiness during application) | ○ | ○ | Δ | Δ |
| Emulsion stability (50° C. × 1M) | ○ | ○ | Δ | Δ |
| Dispersion stability (50° C. × 1M) | ○ | ○ | Δ | Δ |

*1 Tinosorb M: Ciba Specialty Chemicals Inc. [Dispersion solution consisting of 50% of bis-ethylhexyloxyphenol methoxyphenyl triazine, 7.5% of decyl glucoside, 0.2% of xanthan gum, 0.4% of propylene glycol, and 49.4% of water]
*2 PEMULEN TR-2: BF Goodrich (Production Method)
Production Method 2-1:

To a part of Component (1), Components (3), (4) and (8) are added with heat, and the mixture is emulsified with a high-pressure emulsification device (manufactured by APV). Component (5) is added to the emulsion, and then the other components are added and mixed therewith to obtain the aimed O/W emulsified composition.

Production Method 2-1':

Components (6), (7), (8), and a part of Component (1) are mixed, and a dissolved mixture of Components (3) and (4) is added thereto. The obtained mixture is emulsified with a homomixer. Component (5) is added to the emulsion, and then the other components are added and mixed therewith to obtain the aimed O/W emulsified composition.

Production Method 2-2:

A dissolved mixture of Components (3), (4) and (8) is added to a solution in which Component (11) is dissolved in Component (1), and the mixture is emulsified with a homomixer. Component (5) is added to the emulsion, and then the other components are added and mixed therewith to obtain the aimed O/W emulsified composition.

As shown in Table 5, even with the same composition, when the emulsion particle size exceeds 700 nm such as Test examples 5-a to 5-b, stickiness is felt during application on the skin, the emulsion stability is not sufficient, and furthermore the aggregation or precipitation over time of methylene bis-benzotriazolyl tetramethylbutylphenol which has been finely dispersed just after preparation is observed.

Example 6

Amount of Surfactant

O/W emulsified compositions were prepared in the same method with Test Example 5-1, except for changing the amounts of block polymer POE(20)POP(80)cetyl ether as an emulsifier.

TABLE 6

| Components | Test Ex. 5-1 | Test Ex. 6-a | Test Ex 6-b |
|---|---|---|---|
| POE(20)POP(8)cetyl ether | 0.4 | 0.2 | 3.1 |
| Average emulsion particle size | 614 nm | 670 nm | 560 nm |
| Feeling in use(stickiness during application) | ○ | ○ | x |
| Emulsion stability (50° C. × 1M) | ○ | Δ | ○ |
| Dispersion stability (50° C. × 1M) | ○ | ○ | ○ |

As shown in Table 6, the emulsion stability tends to decrease when the amount of block polymer is too small. When the block polymer is contained excessively, sticky feeling is caused during application.

From these results, the amount of block polymer is preferably 0.3 to 3% by mass, more preferably 0.3 to 2% by mass, and particularly preferably 0.3 to 1% by mass, in the O/W emulsified composition of the present invention.

According to the present invention, as shown in Table 6, it is possible that a large amount of oil-soluble organic UV absorber (e.g., 8% by mass or more) is stably emulsified with use of an extremely small amount of emulsifier (e.g., 1% by mass or less) to provide an O/W emulsified composition excellent in UV protection ability, formulation stability, and feeling in use.

Example 7

Kind of Surfactant

O/W emulsified compositions were prepared in the same method with Test example 5-1, except for changing the kinds of block polymer POE(20)POP(80)cetyl ether as an emulsifier.

TABLE 7

| Components | Test Ex. 5-1 | Test Ex. 7-1 | Test Ex. 7-2 | Test Ex. 7-a | Test Ex. 7-b | Test Ex. 7-c |
|---|---|---|---|---|---|---|
| POE(20)POP(8)cetyl ether [HLB = 12.5] | 0.4 | — | — | — | — | — |
| POE(50)POP(40)dimethyl ether [HLB = 17] | — | 0.4 | — | — | — | — |
| POE(35)POP(40)dimethyl ether [HLB = 12] | — | — | 0.4 | — | — | — |
| POE(30)behenyl ether [HLB = 18] | — | — | — | 0.4 | — | — |
| POE(60)glyceryl isostearate [HLB = 18.3] | — | — | — | — | 0.4 | — |
| POE(60)hydrogenated castor oil [HLB = 14.6] | — | — | — | — | — | 0.4 |
| POE(100)hydrogenated castor oil [HLB = 16.5] | — | — | — | — | — | — |

TABLE 7-continued

| | | | | | | |
|---|---|---|---|---|---|---|
| POE(30)phytosterol [HLB = 18] | — | — | — | — | — | — |
| POE(30)cholestanol [HLB = 17] | — | — | — | — | — | — |
| POE(20)sorbitan monostearate [HLB = 14.9] | — | — | — | — | — | — |
| POE(20)sorbitan monolaurate [HLB = 16.9] | — | — | — | — | — | — |
| Average emulsion particle size | 614 nm | 604 nm | 690 nm | 1000 nm | 1500 nm | 2000 nm |
| Feeling in use (stickiness during application) | ○ | ○ | ○ | Δ | Δ | Δ |
| Emulsion stability (50° C. × 1M) | ○ | ○ | ○ | Δ | Δ | Δ |
| Dispersion stability (50° C. × 1M) | ○ | ○ | ○ | Δ | Δ | Δ |

| Components | Test Ex. 7-d | Test Ex. 7-e | Test Ex. 7-f | Test Ex. 7-g | Test Ex. 7-h |
|---|---|---|---|---|---|
| POE(20)POP(8)cetyl ether [HLB = 12.5] | — | — | — | — | — |
| POE(50)POP(40)dimethyl ether [HLB = 17] | — | — | — | — | — |
| POE(35)POP(40)dimethyl ether [HLB = 12] | — | — | — | — | — |
| POE(30)behenyl ether [HLB = 18] | — | — | — | — | — |
| POE(60)glyceryl isostearate [HLB = 18.3] | — | — | — | — | — |
| POE(60)hydrogenated castor oil [HLB = 14.6] | — | — | — | — | — |
| POE(100)hydrogenated castor oil [HLB = 16.5] | 0.4 | — | — | — | — |
| POE(30)phytosterol [HLB = 18] | — | 0.4 | — | — | — |
| POE(30)cholestanol [HLB = 17] | — | — | 0.4 | — | — |
| POE(20)sorbitan monostearate [HLB = 14.9] | — | — | — | 0.4 | — |
| POE(20)sorbitan monolaurate [HLB = 16.9] | — | — | — | — | 0.4 |
| Average emulsion particle size | 1500 nm | 1000 nm | 1100 nm | 3100 nm | 3000 nm |
| Feeling in use (stickiness during application) | Δ | Δ | Δ | x | x |
| Emulsion stability (50° C. × 1M) | Δ | Δ | Δ | x | x |
| Dispersion stability (50° C. × 1M) | Δ | Δ | Δ | x | x |

As shown in Table 7, with the block polymer of the formula (1) or (2), the oil phase containing the component (a) could be easily emulsified to be 700 nm or less, and the O/W emulsified composition excellent in formulation stability and feeling in use could be obtained. However, with the other nonionic surfactants, even when the HLB was in the same range, it was difficult to obtain such an O/W emulsified composition.

Example 8

Amount of Organic UV Absorber

O/W emulsified compositions were prepared in the same method with Test example 5-1, except for changing the amounts of organic UV absorber.

TABLE 8

| Components | Test Ex. 8-a | Test Ex. 8-b | Test Ex. 8-c | Test Ex. 8-d |
|---|---|---|---|---|
| Octocrylene | 11 | 5 | 0.5 | 4 |
| Ethylhexyl methoxycinnamate | 5 | 5 | 4 | 4 |
| Tinosorb M *1 | 8 | 22 | 8 | 0.2 |
| (methylene bis-benzo triazolyl tetramethylbutylphenol) | (4) | (11) | (4) | (0.1) |
| Average emulsion particle size | 680 nm | 620 nm | 470 nm | 600 nm |
| Feeling in use (stickiness during application) | Δ | ○ | ○ | ○ |
| Emulsion stability (50° C. × 1M) | Δ | ○ | ○ | ○ |
| Dispersion stability (50° C. × 1M) | ○ | Δ | ○ | ○ |
| UV protection ability | ○ | ○ | x | x |

As shown in Test examples 8-a to 8-b, when octocrylene is contained excessively, stickiness is caused or the emulsion stability decreases even if the oil phase was emulsified to be 700 nm or less. When methylene bis-benzotriazolyl tetramethylbutylphenol is contained excessively, precipitation over time may be caused.

From these results, in the O/W emulsified composition, it is preferred that the amount of octocrylene is 10% by mass or less, and the amount of methylene bis-benzotriazolyl tetramethylbutylphenol is 10% by mass or less.

In this context, as shown in Test Examples 8-c to 8-d, when the amount of organic UV absorbers is too small, the UV protection ability decreases. Thus, the total amount of organic UV absorbers is preferably 8% by mass or more, more preferably 9% by mass or more, and particularly preferably 10% by mass or more.

Example 9

Incorporation of Poorly Soluble Organic UV Absorber

O/W emulsified compositions were prepared with the compositions in Table 9 according to the following production method. As shown in Table 9, in Test example 9-1, wherein a poorly soluble organic UV absorber (bis-ethylhexyloxyphenol methoxyphenyl triazine) was incorporated in the oil phase of the O/W emulsified composition according to the present invention, the O/W emulsified composition excellent in emulsion stability, dispersion stability, and feeling in use could be obtained. Furthermore, precipitation of bis-ethylhexyloxyphenol methoxyphenyl triazine over time was not observed.

TABLE 9

| No. | Components | Test Ex. 9-1 | Test Ex. 9-a |
|---|---|---|---|
| 1 | Water | Balance | Balance |
| 2 | Ethanol | 6 | 6 |
| 3 | Octocrylene | 5 | 5 |
| 4 | Ethylhexyl methoxycinnamate | 5 | 5 |
| 5 | Bis-ethylhexyloxyphenol methoxyphenyl triazine | 2 | 2 |
| 6 | Tinosorb M *1 | 8 | 8 |
| | (methylene bis-benzo triazolyl tetramethylbutylphenol) | (4) | (4) |
| 7 | Dipropylene glycol | 3 | 3 |
| 8 | Glycerin | 1 | 1 |
| 9 | POE(20)POP(8)cetyl ether | 0.4 | 0.4 |
| 10 | Isostearic acid | 0.2 | 0.2 |
| 11 | Carbomer K | 0.12 | 0.12 |
| 12 | (Acrylic acid/(C10-30)alkyl acrylate) copolymer *2 | 0.06 | 0.06 |

TABLE 9-continued

| | | Production method 3 or 3' | Production method 4 |
|---|---|---|---|
| 13 | Trisodium edetate | 0.02 | 0.02 |
| 14 | BHT | 0.004 | 0.004 |
| 15 | Phenoxyethanol | 0.3 | 0.3 |
| 16 | Methyl paraben | 0.15 | 0.15 |
| Production method | | Production method 3 or 3' | Production method 4 |
| Average emulsion particle size | | 630 nm | 800 nm |
| Feeling in use (stickiness during application) | | ○ | Δ |
| Emulsion stability (50° C. × 1M) | | ○ | x |
| Dispersion stability (50° C. × 1M) | | ○ | x |

(Production Method)
Production Method 3:

To a part of Component (1), Components (3) to (5) and Component (9) are added with heat, and the mixture is emulsified with a high-pressure emulsification device (manufactured by APV). Component (6) is added to the emulsion, and then the other components are added and mixed therewith to obtain the aimed O/W emulsified composition.

Production Method 3':

Components (7), (8), (9), and a part of Component (1) are mixed, and a dissolved mixture of Components (3) to (5) is added thereto. The obtained mixture is emulsified with a homomixer. Component (6) is added to the emulsion, and then the other components are added and mixed therewith to obtain the aimed O/W emulsified composition.

Production Method 4:

A dissolved mixture of Components (3) to (5) and Component (9) is added to a solution in which Component (12) is dissolved in Component (1), and the mixture is emulsified with a homomixer. Component (6) is added to the emulsion, and then the other components are added and mixed therewith to obtain the aimed O/W emulsified composition.

What is claimed is:

1. An oil in water emulsified composition, comprising:
   (a) an organic UV absorber in an oil state at 20° C., comprising (a1) octocrylene that is 1 to 10% by mass in the oil in water emulsified composition;
   (b) an organic UV absorber in a solid state at 20° C., selected from (b1) bis-ethylhexyloxyphenol methoxyphenyl triazine that is 0.5 to 5% by mass in the oil in water emulsified composition and (b2) methylene bis-benzotriazolyl tetrarmethylbutylphenol that is 0.5 to 10% by mass in the oil in water emulsified composition; and
   (c) a polyoxyethylene/polyoxyalkylene alkyl ether block polymer that is 0.3 to 3% by mass in the oil in water emulsified composition and represented by formula (1) or (2):

$$R_1O-(PO)m-(EO)n-H \quad (1)$$

wherein $R_1$ is a hydrocarbon group having 16 to 18 carbon atoms; PO is an oxypropylene group, EO is an oxyethylene group, and PO and EO are added to each other in block form; and m and n respectively represent average addition mole number of PO and EO, $70>m>4$, $70>n>10$, and $n>m$;

$$R_2O-(AO)p-(EO)q-R_3 \quad (2)$$

wherein $R_2$ and $R_3$ are either identical to or different from each other, and each of them is a hydrocarbon group having 1 to 4 carbon atoms; AO is an oxyalkylene group having 3 to 4 carbon atoms, EO is an oxyethylene group, and AO and EO are added to each other in block form; and p and q respectively represent average addition mole number of AO and EO, $1 \leq p \leq 70$, $1 \leq q \leq 70$, and $0.2 < (q/(p+q)) < 0.8$, wherein average particle size of the oil phase comprising the component (a) is 700 nm or less, and wherein when the component (b) comprises the component (b1), the component (a) further comprises (a2) ethylhexyl methoxycinnamate that is 1 to 7.5% by mass in the oil in water emulsified composition.

2. The oil in water emulsified composition according to claim 1, wherein:
   the component (b) comprises the component (b1) bis-ethylhexyloxyphenol methoxyphenyl triazine; and
   the components (a) and (b1) are dissolved in the oil phase.

3. The oil in water emulsified composition according to claim 1, wherein:
   the component (b) comprises the component (b2) methylene bis-benzotriazolyl tetramethylbutylphenol; and
   the component (b2) is dispersed in the aqueous phase.

4. The oil in water emulsified composition according to claim 3, wherein, as the component (b2), an aqueous dispersion wherein methylene bis-benzotriazolyl tetramethylbutylphenol is finely dispersed with alkylpolyglucoside is used.

5. The oil in water emulsified composition according to claim 3, wherein the component (a) further comprises the component (a2) ethylhexyl methoxycinnamate that is 1 to 7.5% by mass in the oil in water emulsified composition.

6. The oil in water emulsified composition according to claim 3, wherein:
   the component (b) further comprises the component (b1) bis-ethylhexyloxyphenol methoxyphenyl triazine; and
   the component (b1) is dissolved in the oil phase.

7. The oil in water emulsified composition according to claim 1, wherein the organic UV absorbers is 8% by mass or more in total in the composition.

8. A sunscreen cosmetic, consisting of the oil in water emulsified composition according to claim 1.

9. A sunscreen cosmetic, consisting of the oil in water emulsified composition according to claim 2.

10. A sunscreen cosmetic, consisting of the oil in water emulsified composition according to claim 3.

11. A sunscreen cosmetic, consisting of the oil in water emulsified composition according to claim 4.

12. A sunscreen cosmetic, consisting of the oil in water emulsified composition according to claim 5.

13. A sunscreen cosmetic, consisting of the oil in water emulsified composition according to claim 6.

14. A sunscreen cosmetic, consisting of the oil in water emulsified composition according to claim 7.

* * * * *